United States Patent
Kriznik et al.

(10) Patent No.: US 11,661,446 B2
(45) Date of Patent: May 30, 2023

(54) METHOD FOR THE AFFINITY PURIFICATION OF RECOMBINANT PROTEINS BASED ON THE LECTIN ACTIVITY OF THE CRD OF A GALECTIN

(71) Applicants: UNIVERSITÉ DE LORRAINE, Nancy (FR); CENTRE HOSPITALIER RÉGIONAL DE NANCY, Nancy (FR)

(72) Inventors: Alexandre Kriznik, Villers-lès-Nancy (FR); Pascal Saim Reboul, Vandoeuvre-lès-Nancy (FR); Mélissa Jenner Yelehe-Okouma, Jarville-la-Malgrange (FR)

(73) Assignees: UNIVERSITÉ DE LORRAINE, Nancy (FR); CENTRE HOSPITALIER RÉGIONAL DE NANCY, Nancy (FR)

( * ) Notice: Subject to any disclaimer, the term of this patent is extended or adjusted under 35 U.S.C. 154(b) by 311 days.

(21) Appl. No.: 16/301,312

(22) PCT Filed: May 11, 2017

(86) PCT No.: PCT/FR2017/051140
§ 371 (c)(1),
(2) Date: Jun. 18, 2019

(87) PCT Pub. No.: WO2017/194888
PCT Pub. Date: Nov. 16, 2017

(65) Prior Publication Data
US 2019/0359665 A1   Nov. 28, 2019

(30) Foreign Application Priority Data
May 13, 2016  (FR) ..................................... 1654324

(51) Int. Cl.
| | | |
|---|---|---|
| *C07K 14/47* | (2006.01) | |
| *C07K 1/22* | (2006.01) | |
| *C07K 14/705* | (2006.01) | |
| *C12N 9/04* | (2006.01) | |
| *C12N 15/70* | (2006.01) | |

(52) U.S. Cl.
CPC ............ *C07K 14/4726* (2013.01); *C07K 1/22* (2013.01); *C07K 14/70503* (2013.01); *C12N 9/0006* (2013.01); *C12N 15/70* (2013.01); *C07K 2319/20* (2013.01); *C07K 2319/50* (2013.01)

(58) Field of Classification Search
CPC .................. C07K 14/4726; C07K 1/22; C07K 14/70503; C07K 2319/20; C07K 2319/50; C07K 14/245; C07K 14/7056; C12N 9/0006; C12N 15/70
See application file for complete search history.

(56) References Cited

U.S. PATENT DOCUMENTS

| | | | |
|---|---|---|---|
| 2004/0023855 A1 * | 2/2004 | John ........................ | B82Y 5/00 424/130.1 |
| 2009/0280535 A1 | 11/2009 | Wang | |
| 2012/0114674 A1 | 5/2012 | Renner et al. | |

OTHER PUBLICATIONS

Pasek et al, Galectin-1 as a fusion partner for the production of soluble and folded human b-1,4-galactosyltransferase-T7 in E. coli. Biochem Biophys Res Commun. Apr. 9, 2010;394(3):679-84.*
NCBI BLAST of SID 1 from John et al, US2004/0023855. Alignment with SID 3 herein.*
Day et al, Eph/Ephrin membrane proteins: a mammalian expression vector pTlg-BOS-Fc allowing rapid protein purification. Protein Pept Lett. 2006;13(2):193-6.*
Jenny et al, A critical review of the methods for cleavage of fusion proteins with thrombin and factor Xa. Protein Expr Purif. Sep. 2003;31(1):1-11. Review.*
Gen Bank Accession No. PDB 6H64_A, published Jun. 19, 2021 (Year: 2021).*
GenBank Accession No. AF196329.1, "Homo sapiens triggering receptor expressed on monocytes 1 mRNA, complete cds", May 24, 2000.
Matthew S. Kelker et al., "Crystal Structure of Mouse Triggering Receptor Expressed on Myeloid Cells 1 (TREM-1) at 1.47 Å", J. Mol. Biol. (2004) 342(4): 1237-1248. (Abstract Only).
Matthew S. Kelker et al., "Crystal Structure of Mouse Triggering Receptor Expressed on Myeloid Cells 1 (TREM-1) at 1.76 Å", J. Mol. Biol. (2004) 344: 1175-1181. (Full Text).
Sergei Radaev et al., "Crystal Structure of Human Myeloid Cell Activating Receptor TREM-1", Structure (2003), 11:1527-1535. (Full Text).
Taylor, M. E., et al., "Carbohydrate-recognition domains as tools for rapid purification of recombinant eukaryotic proteins," Biochem. J. 1991;274:575-580.
Zdanov, A. S., et al., "Tobacco Etch Virus Protease: Crystal Structure of the Active Enzyme and Its Inactive Mutant," SpringerLink 2003, vol. 29, retrieved from the Internet: URL:http://link.springer.com/article/10.1023/A:1026041223534 [retrieved on Sep. 20, 2016], abstract.
Miller, M. C., et al., "Binding of polysaccharides to human galectin-3 at a noncanonical site in its carbohydrate recognition domain," Gycobiology 2016;26(1):88-99.
Dumic, J., et al., "Galectin-3: An open-ended story," Biochimica et Biophysica Acta 2006;1760:616-635.

(Continued)

*Primary Examiner* — Ganapathirama Raghu
(74) *Attorney, Agent, or Firm* — Kenealy Vaidya LLP

(57) ABSTRACT

The present invention relates to a novel method for the affinity purification of proteins of interest in a single step, based on the lectin activity of the CRD (Carbohydrate Recognition Domain) of a galectin or part of said domain retaining the ability to bind β-galactosidase derivative.

8 Claims, 7 Drawing Sheets
Specification includes a Sequence Listing.

(56) References Cited

OTHER PUBLICATIONS

Hirabayashi, J., et al., "Oligosaccharide specificity of galectins: a search by frontal affinity chromatography," Biochimica et Biophysica Acta 2002;1572:232-254.
International Search Report and Written Opinion for PCT Patent App. No. PCT/FR2017/051140 (dated Jul. 20, 2017).

* cited by examiner

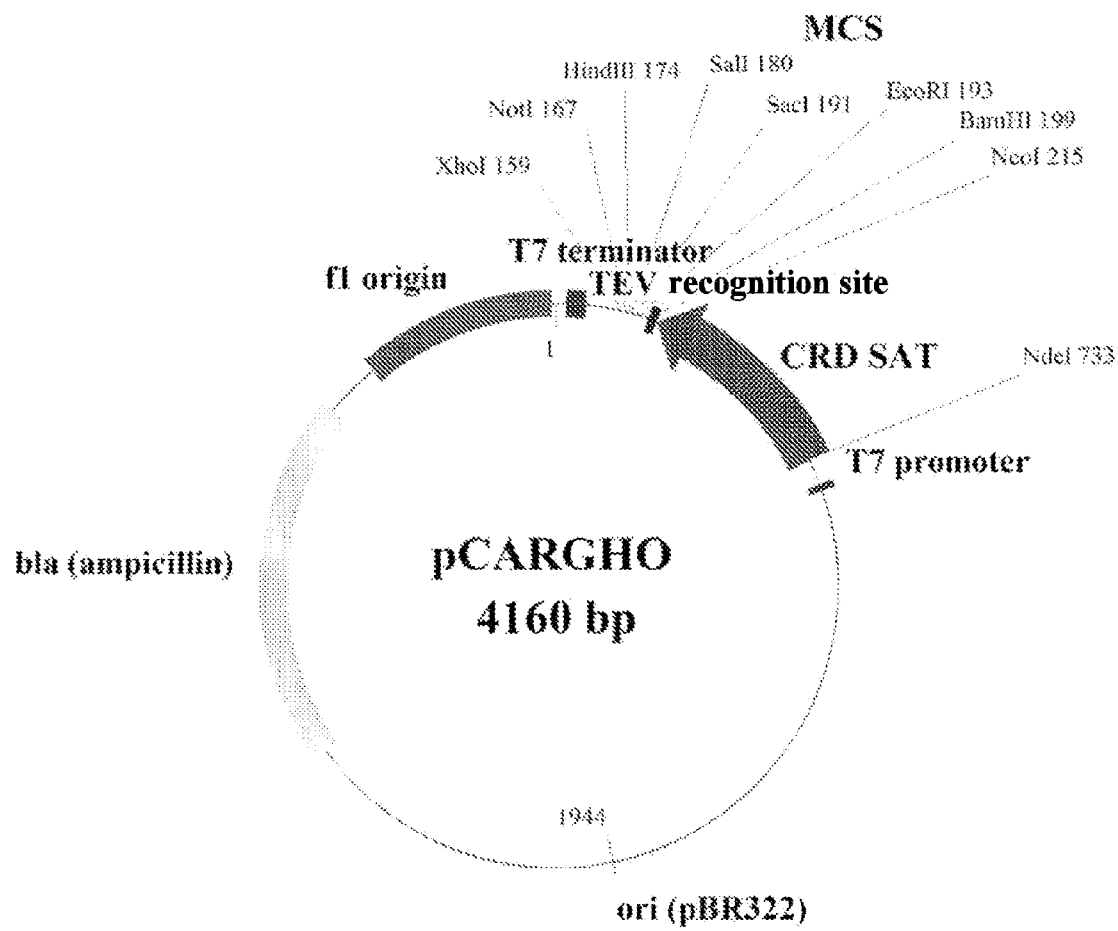
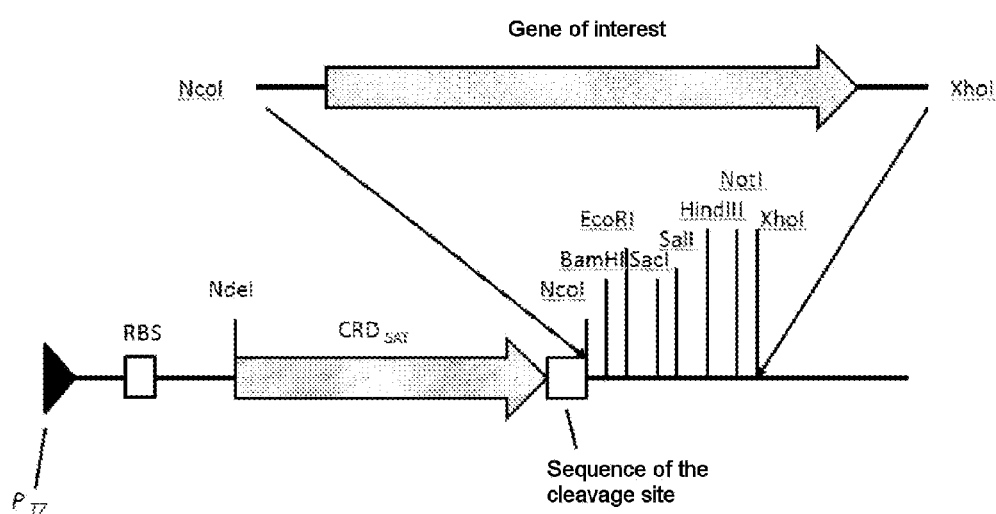
Figure 1

```
                                    T7 promoteur
3335  ctc gat ccc gcg aaa tta ata cga ctc act ata ggg aga cca caa  3376

RBS
3380  cgg ttt ccc tct aga aat aat ttt gtt taa ctt taa gaa gga gat  3421

NdeI  début du CRD_SAT
3425  ata CAT ATG AGC GCA ACC GGT GCA TAT CCG GCA ACC GGT CCG TAT  3466
              Met Ser Ala Thr Gly Ala Tyr Pro Ala Thr Gly Pro Tyr 3470  GGT GCA CCG GCA GGT CCG CTG ATT GTT CCG TAT AAT CTG CCG CTG  3511
      Gly Ala Pro Ala Gly Pro Leu Ile Val Pro Tyr Asn Leu Pro Leu 3515  CCT GGT GGT GTT GTT CCG AAA ATG CTG ATT ACC ATT CTG GGC ACC  3556
      Pro Gly Gly Val Val Pro Lys Met Leu Ile Thr Ile Leu Gly Thr 3560  GTT AAA CCG AAT GCA AAT CGT ATT GCA CTG GAT TTT CAG CGT GGT  3601
      Val Lys Pro Asn Ala Asn Arg Ile Ala Leu Asp Phe Gln Arg Gly 3605  AAT GAT GTG GCC TTT CAT TTT AAT CCG CGT TTC AAT GAA AAC AAC  3646
      Asn Asp Val Ala Phe His Phe Asn Pro Arg Phe Asn Glu Asn Asn 3650  CGT CGT GTT ATT GTG TGC AAT ACC AAA CTG GAT AAC AAT TGG GGT  3691
      Arg Arg Val Ile Val Cys Asn Thr Lys Leu Asp Asn Asn Trp Gly 3695  CGT GAA GAA CGT CAG AGC GTT TTT CCG TTT GAA AGC GGT AAA CCG  3736
      Arg Glu Glu Arg Gln Ser Val Phe Pro Phe Glu Ser Gly Lys Pro 3740  TTT AAA ATC CAG GTT CTG GTT GAA CCG GAT CAT TTT AAA GTT GCA  3781
      Phe Lys Ile Gln Val Leu Val Glu Pro Asp His Phe Lys Val Ala 3785  GTT AAT GAT GCA CAT CTG CTG CAG TAT AAT CAC CGT GTG AAA AAA  3826
      Val Asn Asp Ala His Leu Leu Gln Tyr Asn His Arg Val Lys Lys 3830  CTG AAC GAG ATT AGC AAA CTG GGT ATC AGC GGT GAT ATT GAT CTG  3871
      Leu Asn Glu Ile Ser Lys Leu Gly Ile Ser Gly Asp Ile Asp Leu Fin du CRD_SAT     Bras espaceur
3875  ACC AGC ACC AGC TAT ACC ATG ATT AGC AGC GGT GTT GAT CTG GGT  3916
      Thr Ser Thr Ser Tyr Thr Met Ile Ser Ser Gly Val Asp Leu Gly Séquence reconnue par la protéase TEV    NcoI   EcoRV   BamHI
3920  ACA GAA AAT CTG TAT TTT CAG AGC GCC ATG GAT ATC AAT TCG GAT  3961
      Thr Glu Asn Leu Tyr Phe Gln Ser Ala Met Asp Ile Asn Ser Asp
              Site de coupure TEV
                                           MCS EcoRI   SacI    SalI   HindIII  NotI        XhoI
3965  CCG AAT TCG AGC TCC GTC GAC AAG CTT GCG GCC GCA CTC gag cac  4006
      Pro Asn Ser Ser Ser Val Asp Lys Leu Ala Ala Ala Leu Glu His Polyhistidine tag (x6)
4010  cac cac cac cac cac tga gat ccg gct gct aac aaa gcc gaa g    4051
      His His His His His End 4055  gaa gct gag ttg gct gct gcc acc gct gag caa taa cta gca taa  4096
                    T7 terminateur
4100  ccc ctt ggg gcc tct aaa cgg gtc ttg agg ggt ttt tgc tga aa   4141
```

Figure 2

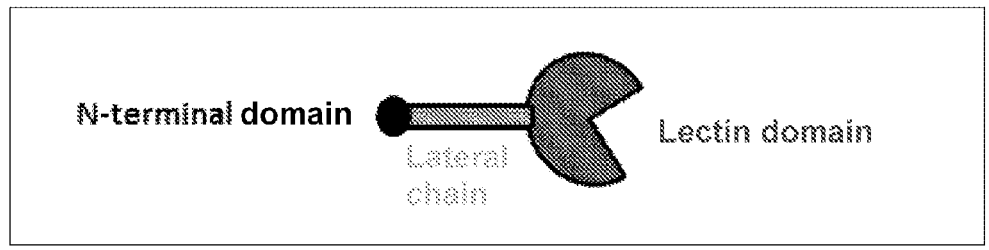

| *N-terminal domain* | Lateral chain | Lectin domain (CRD) |
|---|---|---|
| SAT Start of CRD<sub>SAT</sub> | GGVVP Start of CRD<sub>GGVVP</sub> | LITIL Start of CRD<sub>LITIL</sub> |

Figure 4

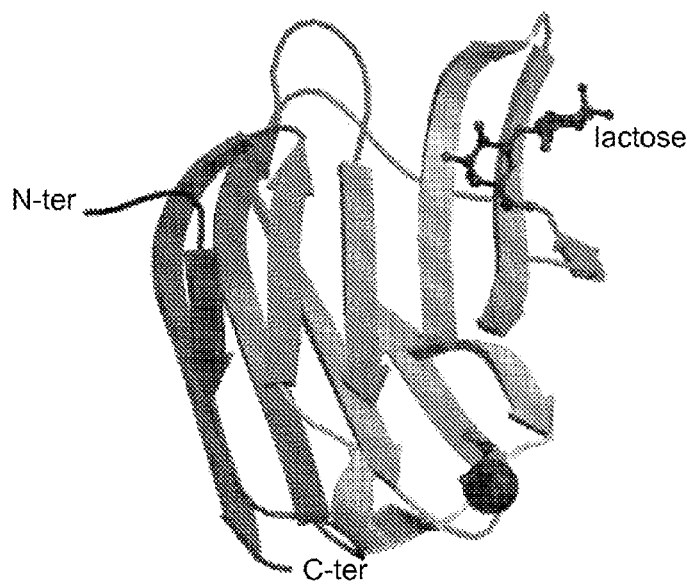

Figure 5

```
Homo sapiens        1  SAPGAYPATGPYGAPAGPFLIVFTNLPLPGGNVPFRALITILGTVKFNAAPIALDFQKNGVAHFNFRFNNRPVIVCNTFLRNWGREEKQSVPFFESG
Gorilla gorilla     1  SAPGAYPATGPYGAPAGPFLIVFTNLPLPLRGGYVPFRALITILGTVKFNAAMKIALDFQKNIVAFHFNPKFNEKANRVIVCNTKLRNWGRERQSVPFFESG
Felis catus         1  SAPGSYPAAGPFVPFAGPFYGIPSGPLNVFYDLPLPFPGSGIRFRMLITILGTVKFNSANRLLLHYKNGBDVAPHFNPFFHEDNKRVIVCNTRLEKLRGNEERQSTFPFFES.
Bos taurus          1  SAPGSYPAAGPYGIPSGPINVFYDLPLPFPGSGIRFRMLITILGTVKFNSANRLLLHYKNGBDVAPHFNPFFHEDNKRVIVCNTRLEKLRGNEERQSTFPFFES.
Mus musculus        1  SAPGGYPAAGPFYVPAGPFLIVPYDLPLPQRGVNFPPLITIMGHVKFNPARRIVLFRRGHDVAHFHFNPNRFNENNRPVIVCNTPQDMNGCKFRRQGAYFFESG
Rattus norvegicus   1  SAPGAYPATGPFGAPFGELIVPYDMFLPGGVNFRALITILGNVRFMANSITLNFKQNDIAFHFPRNEMMFRVIVCNTPQNNNWRFESNQSAYFFESG
consensus           1  ** .**** ** .  .*** *** . *** *********.*.********   ** .. ***.****  *.******.* **** .*** .    .******

Homo sapiens      101  KPFKIQVINEPDBFKVAVNDARLLQYNBRVFKILNEISPKLGTSGDIDIFSASYTNI        SEQ ID NO : 1
Gorilla gorilla   101  KPFKIQVLNEPDKFKVAVNDAKILQYNBPVAKILNEISRIAGSGDIDIFSASYNMI        SEQ ID NO : 7
Felis catus       101  KPFKIQVLVESDNFKVAVNDAEILQTNRFMRNLHELSKLGTSGJDLDIFSASHTMI        SEQ ID NO : 8
Bos taurus        101  KPFKIQVLVFFDHFKVAVRBALLQYNHRVSNFGEISTLGISGFITLGSASHTMI        SEQ ID NO : 9
Mus musculus      101  KPFKIQVLVEADHFKVAVMEARLLREISQLGISGDISANHHAMI                   SEQ ID NO : 10
Rattus norvegicus 101  KPFKIQVLVEADHFVAVNEVRLLQYNERMKDHLRGISQLGIIGDITHSASHAMI          SEQ ID NO : 11
consensus         101  ********.*. *****.***.* ..****.***.*** ****...**

Sequences (1:2) Aligned. Score: 98.7%
Sequences (1:3) Aligned. Score: 87.0%
Sequences (1:4) Aligned. Score: 85.8%
Sequences (1:5) Aligned. Score: 85.8%
Sequences (1:6) Aligned. Score: 83.8%
```

Figure 9

SEQUENCE LISTING

<160> NUMBER OF SEQ ID NOS: 12

<210> SEQ ID NO 1
<211> LENGTH: 157
<212> TYPE: PRT
<213> ORGANISM: Homo sapiens
<220> FEATURE:
<221> NAME/KEY: SITE
<222> LOCATION: (1)..(1)
<223> OTHER INFORMATION: Xaa is methionine or nothing
<220> FEATURE:
<221> NAME/KEY: SITE
<222> LOCATION: (2)..(2)
<223> OTHER INFORMATION: Xaa is glycine, or nothing in the optimized
      version of CRDSAT
<220> FEATURE:
<221> NAME/KEY: SITE
<222> LOCATION: (36)..(36)
<223> OTHER INFORMATION: Xaa is arginine, or lysine in the optimized
      version of CRDSAT
<220> FEATURE:
<221> NAME/KEY: SITE
<222> LOCATION: (152)..(152)
<223> OTHER INFORMATION: Xaa is alanine, or threonine in the optimized
      version of CRDSAT

<400> SEQUENCE: 1

Xaa Xaa Ser Ala Thr Gly Ala Tyr Pro Ala Thr Gly Pro Tyr Gly Ala
1               5                   10                  15

Pro Ala Gly Pro Leu Ile Val Pro Tyr Asn Leu Pro Leu Pro Gly Gly
            20                  25                  30

Val Val Pro Xaa Met Leu Ile Thr Ile Leu Gly Thr Val Lys Pro Asn
        35                  40                  45

Ala Asn Arg Ile Ala Leu Asp Phe Gln Arg Gly Asn Asp Val Ala Phe
    50                  55                  60

His Phe Asn Pro Arg Phe Asn Glu Asn Asn Arg Arg Val Ile Val Cys
65                  70                  75                  80

Asn Thr Lys Leu Asp Asn Asn Trp Gly Arg Glu Glu Arg Gln Ser Val
                85                  90                  95

Phe Pro Phe Glu Ser Gly Lys Pro Phe Lys Ile Gln Val Leu Val Glu
            100                 105                 110

Pro Asp His Phe Lys Val Ala Val Asn Asp Ala His Leu Leu Gln Tyr
        115                 120                 125

Asn His Arg Val Lys Lys Leu Asn Glu Ile Ser Lys Leu Gly Ile Ser
    130                 135                 140

Gly Asp Ile Asp Leu Thr Ser Xaa Ser Tyr Thr Met Ile
145                 150                 155

<210> SEQ ID NO 2
<211> LENGTH: 807
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Partial sequence of the pCARGHO vector
<220> FEATURE:
<221> NAME/KEY: CDS
<222> LOCATION: (94)..(690)

<400> SEQUENCE: 2
gatcccgcga aattaatacg actcactata gggagaccac aacggtttcc ctctagaaat       60
aattttgttt aactttaaga aggagatata cat atg agc gca acc ggt gca tat      114
                                    Met Ser Ala Thr Gly Ala Tyr

|  |  |  |  |  |  |  |  |  |  |  |  |  |  |  |  |
|---|---|---|---|---|---|---|---|---|---|---|---|---|---|---|---|
| ccg | gca | acc | ggt | ccg | tat | ggt | gca | ccg | gca | ggt | ccg | ctg | att | gtt | ccg | 162
| Pro | Ala | Thr | Gly | Pro | Tyr | Gly | Ala | Pro | Ala | Gly | Pro | Leu | Ile | Val | Pro |
|  |  | 10 |  |  |  |  | 15 |  |  |  |  | 20 |  |  |  |

```
                1               5
ccg gca acc ggt ccg tat ggt gca ccg gca ggt ccg ctg att gtt ccg     162
Pro Ala Thr Gly Pro Tyr Gly Ala Pro Ala Gly Pro Leu Ile Val Pro
        10              15              20 tat aat ctg ccg ctg cct ggt ggt gtt gtt ccg aaa atg ctg att acc     210
Tyr Asn Leu Pro Leu Pro Gly Gly Val Val Pro Lys Met Leu Ile Thr
    25              30              35 att ctg ggc acc gtt aaa ccg aat gca aat cgt att gca ctg gat ttt     258
Ile Leu Gly Thr Val Lys Pro Asn Ala Asn Arg Ile Ala Leu Asp Phe
40              45              50              55 cag cgt ggt aat gat gtg gcc ttt cat ttt aat ccg cgt ttc aat gaa     306
Gln Arg Gly Asn Asp Val Ala Phe His Phe Asn Pro Arg Phe Asn Glu
                60              65              70 aac aac cgt cgt gtt att gtg tgc aat acc aaa ctg gat aac aat tgg     354
Asn Asn Arg Arg Val Ile Val Cys Asn Thr Lys Leu Asp Asn Asn Trp
            75              80              85 ggt cgt gaa gaa cgt cag agc gtt ttt ccg ttt gaa agc ggt aaa ccg     402
Gly Arg Glu Glu Arg Gln Ser Val Phe Pro Phe Glu Ser Gly Lys Pro
        90              95              100 ttt aaa atc cag gtt ctg gtt gaa ccg gat cat ttt aaa gtt gca gtt     450
Phe Lys Ile Gln Val Leu Val Glu Pro Asp His Phe Lys Val Ala Val
    105             110             115 aat gat gca cat ctg ctg cag tat aat cac cgt gtg aaa aaa ctg aac     498
Asn Asp Ala His Leu Leu Gln Tyr Asn His Arg Val Lys Lys Leu Asn
120             125             130             135 gag att agc aaa ctg ggt atc agc ggt gat att gat ctg acc agc acc     546
Glu Ile Ser Lys Leu Gly Ile Ser Gly Asp Ile Asp Leu Thr Ser Thr
                140             145             150 agc tat acc atg att agc agc ggt gtt gat ctg ggt aca gaa aat ctg     594
Ser Tyr Thr Met Ile Ser Ser Gly Val Asp Leu Gly Thr Glu Asn Leu
            155             160             165 tat ttt cag agc gcc atg gat atc aat tcg gat ccg aat tcg agc tcc     642
Tyr Phe Gln Ser Ala Met Asp Ile Asn Ser Asp Pro Asn Ser Ser Ser
        170             175             180 gtc gac aag ctt gcg gcc gca ctc gag cac cac cac cac cac cac tga     690
Val Asp Lys Leu Ala Ala Ala Leu Glu His His His His His His
    185             190             195 gatccggctg ctaacaaagc ccgaaaggaa gctgagttgg ctgctgccac cgctgagcaa     750
taactagcat aaccccttgg ggcctctaaa cgggtcttga ggggttttttt gctgaaa       807
```

<210> SEQ ID NO 3
<211> LENGTH: 198
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Synthetic Construct

<400> SEQUENCE: 3

Met Ser Ala Thr Gly Ala Tyr Pro Ala Thr Gly Pro Tyr Gly Ala Pro
1               5                   10                  15

Ala Gly Pro Leu Ile Val Pro Tyr Asn Leu Pro Leu Pro Gly Gly Val
            20                  25                  30

Val Pro Lys Met Leu Ile Thr Ile Leu Gly Thr Val Lys Pro Asn Ala
        35                  40                  45

Asn Arg Ile Ala Leu Asp Phe Gln Arg Gly Asn Asp Val Ala Phe His
    50                  55                  60

```
Phe Asn Pro Arg Phe Asn Glu Asn Asn Arg Arg Val Ile Val Cys Asn
 65                  70                  75                  80

Thr Lys Leu Asp Asn Asn Trp Gly Arg Glu Glu Arg Gln Ser Val Phe
                 85                  90                  95

Pro Phe Glu Ser Gly Lys Pro Phe Lys Ile Gln Val Leu Val Glu Pro
            100                 105                 110

Asp His Phe Lys Val Ala Val Asn Asp Ala His Leu Leu Gln Tyr Asn
        115                 120                 125

His Arg Val Lys Lys Leu Asn Glu Ile Ser Lys Leu Gly Ile Ser Gly
    130                 135                 140

Asp Ile Asp Leu Thr Ser Thr Ser Tyr Thr Met Ile Ser Ser Gly Val
145                 150                 155                 160

Asp Leu Gly Thr Glu Asn Leu Tyr Phe Gln Ser Ala Met Asp Ile Asn
                165                 170                 175

Ser Asp Pro Asn Ser Ser Ser Val Asp Lys Leu Ala Ala Ala Leu Glu
            180                 185                 190

His His His His His His
        195
```

```
<210> SEQ ID NO 4
<211> LENGTH: 250
<212> TYPE: PRT
<213> ORGANISM: Homo sapiens

<400> SEQUENCE: 4

Met Ala Asp Asn Phe Ser Leu His Asp Ala Leu Ser Gly Ser Gly Asn
 1               5                  10                  15

Pro Asn Pro Gln Gly Trp Pro Gly Ala Trp Gly Asn Gln Pro Ala Gly
                20                  25                  30

Ala Gly Gly Tyr Pro Gly Ala Ser Tyr Pro Gly Ala Tyr Pro Gly Gln
            35                  40                  45

Ala Pro Pro Gly Ala Tyr Pro Gly Gln Ala Pro Pro Gly Ala Tyr Pro
 50                  55                  60

Gly Ala Pro Gly Ala Tyr Pro Gly Ala Pro Ala Pro Gly Val Tyr Pro
 65                  70                  75                  80

Gly Pro Pro Ser Gly Pro Gly Ala Tyr Pro Ser Ser Gly Gln Pro Ser
                 85                 90                  95

Ala Thr Gly Ala Tyr Pro Ala Thr Gly Pro Tyr Gly Ala Pro Ala Gly
            100                 105                 110

Pro Leu Ile Val Pro Tyr Asn Leu Pro Leu Pro Gly Gly Val Val Pro
        115                 120                 125

Arg Met Leu Ile Thr Ile Leu Gly Thr Val Lys Pro Asn Ala Asn Arg
    130                 135                 140

Ile Ala Leu Asp Phe Gln Arg Gly Asn Asp Val Ala Phe His Phe Asn
145                 150                 155                 160

Pro Arg Phe Asn Glu Asn Asn Arg Arg Val Ile Val Cys Asn Thr Lys
                165                 170                 175

Leu Asp Asn Asn Trp Gly Arg Glu Glu Arg Gln Ser Val Phe Pro Phe
            180                 185                 190

Glu Ser Gly Lys Pro Phe Lys Ile Gln Val Leu Val Glu Pro Asp His
        195                 200                 205

Phe Lys Val Ala Val Asn Asp Ala His Leu Leu Gln Tyr Asn His Arg
    210                 215                 220

Val Lys Lys Leu Asn Glu Ile Ser Lys Leu Gly Ile Ser Gly Asp Ile
225                 230                 235                 240
```

```
Asp Leu Thr Ser Thr Ser Tyr Thr Met Ile
                245                 250

<210> SEQ ID NO 5
<211> LENGTH: 5
<212> TYPE: PRT
<213> ORGANISM: Homo sapiens

<400> SEQUENCE: 5

Gly Gly Val Val Pro
1               5

<210> SEQ ID NO 6
<211> LENGTH: 5
<212> TYPE: PRT
<213> ORGANISM: Homo sapiens

<400> SEQUENCE: 6

Leu Ile Thr Ile Leu
1               5

<210> SEQ ID NO 7
<211> LENGTH: 155
<212> TYPE: PRT
<213> ORGANISM: Gorilla gorilla

<400> SEQUENCE: 7

Ser Ala Pro Gly Ala Tyr Pro Ala Thr Gly Pro Tyr Gly Ala Pro Ala
1               5                   10                  15

Gly Pro Leu Ile Val Pro Tyr Asn Leu Pro Leu Pro Gly Gly Val Val
                20                  25                  30

Pro Arg Met Leu Ile Thr Ile Leu Gly Thr Val Lys Pro Asn Ala Asn
            35                  40                  45

Arg Ile Ala Leu Asp Phe Gln Arg Gly Asn Asp Val Ala Phe His Phe
    50                  55                  60

Asn Pro Arg Phe Asn Glu Asn Asn Arg Arg Val Ile Val Cys Asn Thr
65                  70                  75                  80

Lys Leu Asp Asn Asn Trp Gly Arg Glu Glu Arg Gln Ser Val Phe Pro
                85                  90                  95

Phe Glu Ser Gly Lys Pro Phe Lys Ile Gln Val Leu Val Glu Pro Asp
            100                 105                 110

His Phe Lys Val Ala Val Asn Asp Ala His Leu Leu Gln Tyr Asn His
        115                 120                 125

Arg Val Lys Lys Leu Asn Glu Ile Ser Lys Leu Gly Ile Ser Gly Asp
    130                 135                 140

Ile Asp Leu Thr Ser Ala Ser Tyr Asn Met Ile
145                 150                 155

<210> SEQ ID NO 8
<211> LENGTH: 155
<212> TYPE: PRT
<213> ORGANISM: Felis catus

<400> SEQUENCE: 8

Ser Ala Pro Gly Ala Tyr Pro Ala Ala Gly Pro Phe Gly Val Pro Ala
1               5                   10                  15

Gly Pro Leu Thr Val Pro Tyr Asp Leu Pro Leu Pro Gly Gly Val Met
                20                  25                  30

Pro Arg Met Leu Ile Thr Ile Leu Gly Thr Val Lys Pro Asn Ala Asn
```

```
                35                  40                  45

Arg Leu Ala Leu Asp Phe Lys Arg Gly Asn Asp Val Ala Phe His Phe
             50                  55                  60

Asn Pro Arg Phe Asn Glu Asp Asn Lys Arg Val Ile Val Cys Asn Thr
 65                  70                  75                  80

Lys Leu Glu Asn Leu Trp Gly Lys Glu Glu Arg Gln Ser Thr Phe Pro
                 85                  90                  95

Phe Glu Ser Gly Lys Pro Phe Lys Ile Gln Val Leu Val Glu Ser Asp
            100                 105                 110

His Phe Lys Val Ala Val Asn Asp Ala His Leu Leu Gln Tyr Asn His
            115                 120                 125

Arg Met Lys Asn Leu His Glu Ile Ser Lys Leu Gly Ile Ser Gly Asp
        130                 135                 140

Ile Asp Leu Thr Ser Ala Ser His Thr Met Ile
145                 150                 155

<210> SEQ ID NO 9
<211> LENGTH: 155
<212> TYPE: PRT
<213> ORGANISM: Bos taurus

<400> SEQUENCE: 9

Ser Ala Pro Gly Ala Tyr Pro Ala Ala Gly Pro Tyr Gly Ile Pro Ser
1               5                  10                  15

Gly Pro Leu Asn Val Pro Tyr Asp Leu Pro Phe Pro Gly Gly Ile Arg
                20                  25                  30

Pro Arg Met Leu Ile Thr Ile Leu Gly Thr Val Lys Pro Asn Ala Asn
            35                  40                  45

Arg Leu Ala Leu Asp Phe Lys Arg Gly Asn Asp Val Ala Phe His Phe
         50                  55                  60

Asn Pro Arg Phe Asn Glu Asp Asn Arg Arg Val Ile Val Cys Asn Ser
 65                  70                  75                  80

Lys Leu Asn Asn Asn Trp Gly Lys Glu Glu Arg Gln Met Val Phe Pro
                 85                  90                  95

Phe Glu Ser Gly Lys Pro Phe Lys Ile Gln Val Leu Val Glu Pro Asp
            100                 105                 110

His Phe Lys Val Ala Val Asn Asp Ala His Leu Leu Gln Tyr Asn His
            115                 120                 125

Arg Val Lys Asn Phe Gly Glu Ile Ser Thr Leu Gly Ile Ser Gly Asp
        130                 135                 140

Ile Thr Leu Thr Ser Ala Ser His Thr Met Ile
145                 150                 155

<210> SEQ ID NO 10
<211> LENGTH: 155
<212> TYPE: PRT
<213> ORGANISM: Mus musculus

<400> SEQUENCE: 10

Ser Ala Pro Gly Gly Tyr Pro Ala Ala Gly Pro Tyr Gly Val Pro Ala
1               5                  10                  15

Gly Pro Leu Thr Val Pro Tyr Asp Leu Pro Leu Pro Gly Gly Val Met
                20                  25                  30

Pro Arg Met Leu Ile Thr Ile Met Gly Thr Val Lys Pro Asn Ala Asn
            35                  40                  45

Arg Ile Val Leu Asp Phe Arg Arg Gly Asn Asp Val Ala Phe His Phe
```

```
                50                  55                  60
Asn Pro Arg Phe Asn Glu Asn Arg Arg Val Ile Val Cys Asn Thr
 65                  70                  75                  80

Lys Gln Asp Asn Asn Trp Gly Lys Glu Glu Arg Gln Ser Ala Phe Pro
                 85                  90                  95

Phe Glu Ser Gly Lys Pro Phe Lys Ile Gln Val Leu Val Glu Ala Asp
                100                 105                 110

His Phe Lys Val Ala Val Asn Asp Ala His Leu Leu Gln Tyr Asn His
            115                 120                 125

Arg Met Lys Asn Leu Arg Glu Ile Ser Gln Leu Gly Ile Ser Gly Asp
        130                 135                 140

Ile Thr Leu Thr Ser Ala Asn His Ala Met Ile
145                 150                 155

<210> SEQ ID NO 11
<211> LENGTH: 155
<212> TYPE: PRT
<213> ORGANISM: Rattus norvegicus

<400> SEQUENCE: 11

Ser Ala Pro Gly Ala Tyr Pro Ala Thr Gly Pro Phe Gly Ala Pro Thr
 1               5                  10                  15

Gly Pro Leu Thr Val Pro Tyr Asp Met Pro Leu Pro Gly Gly Val Met
                 20                  25                  30

Pro Arg Met Leu Ile Thr Ile Gly Thr Val Lys Pro Asn Ala Asn
             35                  40                  45

Ser Ile Thr Leu Asn Phe Lys Arg Gly Asn Asp Ile Ala Phe His Phe
 50                  55                  60

Asn Pro Arg Phe Asn Glu Asn Asn Arg Arg Val Ile Val Cys Asn Thr
 65                  70                  75                  80

Lys Gln Asp Asn Asn Trp Gly Arg Glu Glu Arg Gln Ser Ala Phe Pro
                 85                  90                  95

Phe Glu Ser Gly Lys Pro Phe Lys Ile Gln Val Leu Val Glu Ala Asp
                100                 105                 110

His Phe Lys Val Ala Val Asn Asp Val His Leu Leu Gln Tyr Asn His
            115                 120                 125

Arg Met Lys Asn Leu Arg Glu Ile Ser Gln Leu Gly Ile Ile Gly Asp
        130                 135                 140

Ile Thr Leu Thr Ser Ala Ser His Ala Met Ile
145                 150                 155

<210> SEQ ID NO 12
<211> LENGTH: 289
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Ser Ala Thr Gly Ala Tyr Pro Ala Thr Gly Pro Tyr Gly Ala Pro
 1               5                  10                  15

Ala Gly Pro Leu Ile Val Pro Tyr Asn Leu Pro Leu Pro Gly Gly Val
                 20                  25                  30

Val Pro Lys Met Leu Ile Thr Ile Leu Gly Thr Val Lys Pro Asn Ala
             35                  40                  45

Asn Arg Ile Ala Leu Asp Phe Gln Arg Gly Asn Asp Val Ala Phe His
```

|  |  |  |  | 50 |  |  |  | 55 |  |  | 60 |  |  |
|---|---|---|---|---|---|---|---|---|---|---|---|---|---|

Phe Asn Pro Arg Phe Asn Glu Asn Asn Arg Arg Val Ile Val Cys Asn
65              70              75              80

Thr Lys Leu Asp Asn Asn Trp Gly Arg Glu Glu Arg Gln Ser Val Phe
            85              90              95

Pro Phe Glu Ser Gly Lys Pro Phe Lys Ile Gln Val Leu Val Glu Pro
            100             105             110

Asp His Phe Lys Val Ala Val Asn Asp Ala His Leu Leu Gln Tyr Asn
        115             120             125

His Arg Val Lys Lys Leu Asn Glu Ile Ser Lys Leu Gly Ile Ser Gly
    130             135             140

Asp Ile Asp Leu Thr Ser Thr Ser Tyr Thr Met Ile Ser Ser Gly Val
145             150             155             160

Asp Leu Gly Thr Glu Asn Leu Tyr Phe Gln Ser Ala Met Ala Thr Lys
            165             170             175

Leu Thr Glu Glu Lys Tyr Glu Leu Lys Glu Gly Gln Thr Leu Asp Val
            180             185             190

Lys Cys Asp Tyr Thr Leu Glu Lys Phe Ala Ser Ser Gln Lys Ala Trp
        195             200             205

Gln Ile Ile Arg Asp Gly Glu Met Pro Lys Thr Leu Ala Cys Thr Glu
    210             215             220

Arg Pro Ser Lys Asn Ser His Pro Val Gln Val Gly Arg Ile Ile Leu
225             230             235             240

Glu Asp Tyr His Asp His Gly Leu Leu Arg Val Arg Met Val Asn Leu
            245             250             255

Gln Val Glu Asp Ser Gly Leu Tyr Gln Cys Val Ile Tyr Gln Pro Pro
            260             265             270

Lys Glu Pro His Met Leu Phe Asp Arg Ile Arg Leu Val Val Thr Lys
        275             280             285

Gly

METHOD FOR THE AFFINITY PURIFICATION OF RECOMBINANT PROTEINS BASED ON THE LECTIN ACTIVITY OF THE CRD OF A GALECTIN

CROSS REFERENCE TO RELATED APPLICATIONS

This application is a national phase filing under 35 C.F.R. § 371 of and claims priority to PCT Patent Application No. PCT/FR2017/051140, filed on May 11, 2017, which claims the priority benefit under 35 U.S.C. § 119 of French Patent Application No. 1654324, filed on May 13, 2016, the contents of each of which are hereby incorporated in their entireties by reference.

SEQUENCE LISTING

The instant application contains a Sequence Listing which has been submitted electronically in ASCII format and is hereby incorporated by reference in its entirety. Said ASCII copy, created on Jan. 12, 2022, is named 5090-0125 SL.txt and is 19,538 bytes in size.

BACKGROUND

Some embodiments relate to a process for single-step purification of recombinant proteins of interest by affinity based on the lectin activity of all or part of the lectin domain, such as the CRD domain (carbohydrate recognition domain), of a galectin.

Some embodiments are applicable to public and private research laboratories and also to the pharmaceutical industry where there is a necessity to produce recombinant proteins with the aim of fundamental studies or for therapeutic benefit.

In the description below, the references between square brackets ([ ]) refer to the list of references presented at the end of the text.

In order to produce, at low cost, pure proteins of interest which are indispensable in numerous life sciences applications, it is essential to produce large amounts of recombinant proteins of interest in a host and to simplify the downstream treatment steps.

There are numerous methods for purifying recombinant proteins of interest natively (without a fusion partner, i.e. tag), but this type of purification remains complex with a low yield and sometimes incomplete purity.

SUMMARY

Thus, methods for expression and purification of recombinant proteins fused to a tag have been proposed. Among the commonly used tags are the histidine tag (composed of at least six histidines), maltose binding protein (MBP) and glutathione S-transferase (GST), the latter two being proteins.

The histidine tag is used in the context of IMAC (immobilized metal affinity) technology. This method can consist of purifying a recombinant protein fused to the histidine tag via the interaction of the imidazole rings with divalent metal ions (mainly nickel) immobilized on a resin. The fusion protein is then eluted with a solution of imidazole. However, due to the low specificity thereof, this purification method systematically leads to co-purification of contaminants and may require subsequent additional steps. In addition, firstly nickel is allergenic, fetotoxic and harmful for the environment, and secondly imidazole is also a fetotoxic and reprotoxic compound. Thus, the possible presence of traces of nickel and imidazole in solutions of recombinant proteins purified by IMAC limits the use thereof for in vitro/in vivo applications. Moreover, processes based on metal ions may lead to modifications of some residues of the proteins purified in this way [1, 2].

As for MBP and GST, they are used to purify recombinant proteins by affinity for amylose or glutathione, respectively. Due to steric hindrance due to the molecular weight of MBP, the fusion proteins are difficult to cleave which may reduce the final production yield of the purified recombinant protein. As for GST, it has a low affinity for the glutathione Sepharose resin [3, 4].

Other methods for expressing proteins of interest enabling easy and effective purification by affinity chromatography on resins at low cost, based on the use of lectins as tag, have been developed. The advantage of lectins is that they specifically and reversibly bind to certain polysaccharides. Indeed, there are several classes of lectins that differ by their amino acid sequence, their three-dimensional structure and also by the nature of the sugar binding site. Thus, methods for expressing and purifying proteins of interest have been developed based on lectins such as the mushroom lectin LSL [5] or discoidin that originates from an amoeba [6] on chromatography columns consisting of Sepharose 4B. However, in these methods, the use of a non-grafted resin leads to a risk of non-specific binding to the resin and thus to contamination by bacterial proteins.

A method for purifying proteins of interest using a resin grafted with mannose recognized by the LecB lectin from *P. aeruginosa* is also known [7]. However, mannose is a sugar with a complex and costly synthesis.

A two-step method for purifying proteins of interest using a fusion protein including the lectin domain of a rat hepatic lectin and a molecule of interest, with a site for cleavage by protease inserted between the two, is also known [13]. It has the drawback of functioning in the presence of cation chelators, which may inhibit the biological activity of proteins of interest.

It may therefore be beneficial to provide methods for expressing and purifying proteins of interest that address or overcome some or all of the drawbacks of the processes of the related art.

In accordance with some embodiments, in order to express hitherto insoluble proteins (produced in the form of inclusion bodies) by improving the solubility thereof, and to purify proteins of interest by affinity, has the advantage of not modifying and/or damaging the activity of the majority of proteins.

Some embodiments are therefore directed to a novel process making it possible to purify recombinant proteins in a single step, with high specificity and a high yield. The process of some embodiments uses the lectin domain of a galectin or part of the domain that retains the ability to bind lactose, for example the $CRD_{SAT}$ domain of a galectin, for example human galectin-3, as fusion partner of the protein of interest. This lectin tag thus enables the purification of the protein of interest in a single affinity chromatography step, using a Sepharose resin grafted with lactose molecules.

Some embodiments are directed to a fusion protein including all or part of the lectin domain of a galectin fused with a protein of interest, via a sequence including a site for cleavage by TEV protease (two possible cleavage options; see FIG. 7).

For the purposes of some embodiments, "lectin domain or GLECT domain" is intended to mean the domain of galectins binding β-galactosyl derivatives, such as, for example, lactose and derivatives thereof, and the activity of which does not depend on divalent cations. The access number in the NCBI Conserved Domain database for the GLECT conserved domain is cd00070.

According to a particular embodiment of the presently disclosed subject matter, the part of the lectin domain used binds lactose; this may be the CRD domain of a galectin, and may be the $CRD_{SAT}$ domain of a galectin, for example including the sequence SEQ ID NO: 1.

The $CRD_{SAT}$ domain is a highly conserved domain (between approximately 83 and 99% sequence homology among mammals) (cf. FIG. 9). It belongs to the GLECT (Galactose-binding LECTin) domain superfamily able to specifically bind β-galactosides such as lactose and derivatives thereof.

Another embodiment is directed to an expression vector for a fusion protein, the vector including the following functionally linked elements:
 a) a promoter placed 5' of the elements b), c) and d) and e) described below;
 b) a sequence encoding all or part of the lectin domain of a galectin;
 c) a sequence encoding a spacer arm containing the site for cleavage by TEV;
 d) a cloning site receiving a sequence encoding a protein of interest;
 e) transcription termination signals.

For the purposes of the some embodiments, "promoter" is intended to mean a cis-acting DNA sequence located 5' of the transcription initiation site of the sequence encoding a polypeptide, to which a DNA sequence of an RNA polymerase can bind and initiate correct transcription, and optionally including activators.

In the expression vector of some embodiments, the sequence corresponding to all or part of the lectin domain of a galectin is for example located nearby, upstream of the cloning site and downstream of the promoter. An alternative is to place the sequence nearby, after the cloning site. In both cases, fusion of the sequence with that of the molecule of interest enables purification on resin. One possible way, the sequence b) encodes a part of the lectin domain that binds lactose, encodes the $CRD_{SAT}$ domain of a galectin, encodes the $CRD_{SAT}$ domain including the sequence SEQ ID NO: 1.

According to a particular embodiment of the present invention, the site for cleavage by protease is recognized by TEV protease.

According to a particular embodiment, the expression vector is the pCARGHO (standing for CArbohydrate Recognition domain of Galectin-3 from *Homo sapiens*) expression vector derived from the pET plasmid.

Another embodiment is directed to a process for producing a purified protein of interest, the process including:
 a) preparing an expression vector according to the presently disclosed subject matter;
 b) transforming a host cell with the expression vector;
 c) culturing the transformed host cell under conditions enabling the expression and translation of the fusion protein including the amino acid sequence of all or part of the lectin domain of the galectin and the amino acid sequence of the protein of interest, the amino acid sequence of all or part of the lectin domain of galectin promoting the dissolution of the protein of interest in host cells; and
 d) isolating the protein of interest from the host cell or from the culture medium.

In the process of some embodiments, the isolation or purification step d) is carried out for example by binding the fusion protein, via the lectin domain of the galectin or part of the domain, to a chromatography support grafted with lactose molecules, possibly to an agarose or Sepharose resin grafted with lactose molecules, then (i) cleavage by protease to remove the lectin domain of the galectin or part of the domain (i.e. sequence tag), elution and separation of the molecule of interest and the protease, or (ii) elution of the fusion protein, cleavage by protease in solution, and separation of the protein of interest and the protease.

According to a particular embodiment, the step of separation of the protease and the protein of interest is carried out by ion exchange chromatography or size exclusion chromatography or hydrophobic interaction chromatography.

Another embodiment is directed to a process for purifying a molecule of interest, the process including:
 Option No. 1:
 a) binding the fusion protein of the presently disclosed subject matter to a chromatography support grafted with lactose molecules, possibly a column of Sepharose or agarose resin grafted with lactose molecules;
 b) cleavage by protease of the fusion protein at the specific cleavage site;
 c) elution of the purified molecule of interest; and
 d) separation of the protease from the protein of interest purified in this way.

According to a particular embodiment of the presently disclosed subject matter, step d) is carried out by ion exchange chromatography or size exclusion chromatography or hydrophobic interaction chromatography.

The lectin domain or part of the domain (i.e. the tag) is eliminated from the column by elution by competition with a lactose solution, and the column is regenerated.
 Option No. 2:
 a) binding the fusion protein of the presently disclosed subject matter to a chromatography support grafted with lactose molecules, possibly a column of Sepharose or agarose resin grafted with lactose molecules;
 b) elution of the fusion protein by competition with a lactose solution;
 c) cleavage by protease of the fusion protein at the specific site, in solution;
 d) separation of the lectin domain or part of the domain (i.e. the tag) and the TEV protease from the molecule of interest purified in this way.

According to a particular embodiment of the presently disclosed subject matter, step d) is carried out by ion exchange chromatography or size exclusion chromatography.

Some embodiments directed to the process have the advantage of not using any toxic, carcinogenic or teratogenic compounds. In addition, the lectin activity of the CRD domain of the galectin-3 is much more specific than all the other purification methods and may require only a single step to obtain a degree of purity greater than 95%. Moreover, the conditions for elution of the fusion protein are optimal for the tag to be cleaved by the TEV protease. There is no limit on accepted reducing agents. The CRD tag, in particular $CRD_{SAT}$, has a very low molecular weight (17.3 kDa, 18.8 kDa for the form obtained after cleavage by the TEV protease), which enables the easy elimination thereof by size exclusion chromatography. In addition, it is predominantly constructed of β sheets, affording it a very high degree of stability. Finally, its isoelectric point is highly basic (pI=9.3, pI=8.7 for the form obtained after cleavage by the TEV protease), enabling the easy capture thereof on a cation exchange column. It is possible to jointly eliminate the CRD and the TEV protease, the isoelectric point of which is also basic (pI=8.8) by binding them on a cation exchange column. The protein of interest is then eluted pure in the fraction not retained by the resin (FIG. 10).

Some embodiments are directed to the $CRD_{SAT}$ fusion partner (or tag) derived from a galectin. The amino acid sequence of the $CRD_{SAT}$ domain includes the sequence SEQ ID NO: 1, in which the amino acid in position 36 may be an arginine or a lysine, and/or in which the amino acid in position 152 may be an alanine or a threonine. The CRD fusion partner also has the property of solubilizing proteins described as insoluble, hitherto obtained after long and tedious renaturation of inclusion bodies in urea or guanidium chloride; for example, the human membrane receptor TREM-1 and more particularly the extracellular domain thereof [14-15].

DESCRIPTION OF THE FIGURES

FIG. 1 depicts a circular and linear diagram of the pCARGHO vector.

FIG. 2 depicts the main features of the pCARGHO vector (SEQ ID NOs: 2 and 3).

FIG. 3 depicts a schematic structure of human galectin-3.

FIG. 4 depicts the protein sequence of human galectin-3 and of the 3 CRDs designed (SEQ ID NO: 4).

FIG. 5 depicts the 3D structure of the lectin CRD domain of the galectin-3 interacting with lactose.

FIG. 9 depicts an amino acid sequence alignment of the $CRD_{SAT}$ domain of galectin-3 in different mammals, and also the consensus sequence of the $CRD_{SAT}$ domain.

DETAILED DESCRIPTION

Example 1: Researching the Optimal Form of Truncated Human Galectin-3: Monitoring Purification of 3 Truncated Forms by Lactose Affinity Chromatography Galectin-3

Galectin-3 is an animal lectin of 243 to 286 amino acids depending on the species (Cooper, Biochim. & Biophys. Acta, 1572(2-3): 209-231, 2002) [8]. It is approximately 30 kDa and is composed of a small N-terminal domain, a lateral chain and a C-terminal lectin domain (CRD: Carbohydrate Recognition Domain) (FIGS. 3 and 4) (Leffler et al., Glycoconj. J., 19: 433-440, 2004; Ochieng et al., Biochim. & Biophys. Acta, 1379: 97-106, 1998) [9, 10]. Formed of several beta sheets (Salomonsson et al., J. Biol. Chem., 285: 35079-35091, 2010; Seetharaman et al., J. Biol. Chem., 273: 13047-13052, 1998) [11, 12], the lectin domain enables the protein to interact with molecules containing β-galactoside residues, for example lactose (FIG. 5).

Given its lectin properties, galectin-3 was able to be purified specifically in a single step by affinity chromatography using an agarose resin grafted with lactose molecules, according to the protocol described previously (FIG. 6).

For this purpose, the galectin-3 (whole form) was expressed in E. coli C41(DE3) bacteria then purified on lactose-agarose column. At each purification step, a sample was taken to be run on acrylamide gel (SDS-PAGE). After electrophoretic migration, the gel was stained with Coomassie Brilliant Blue. A: bacterial extract before passage on lactose affinity column. B: bacterial extract after passage on lactose affinity column. C and D: column washes. E: elution fraction of galectin-3; elution with a solution of PBS+lactose 150 mM.

Figure 6:
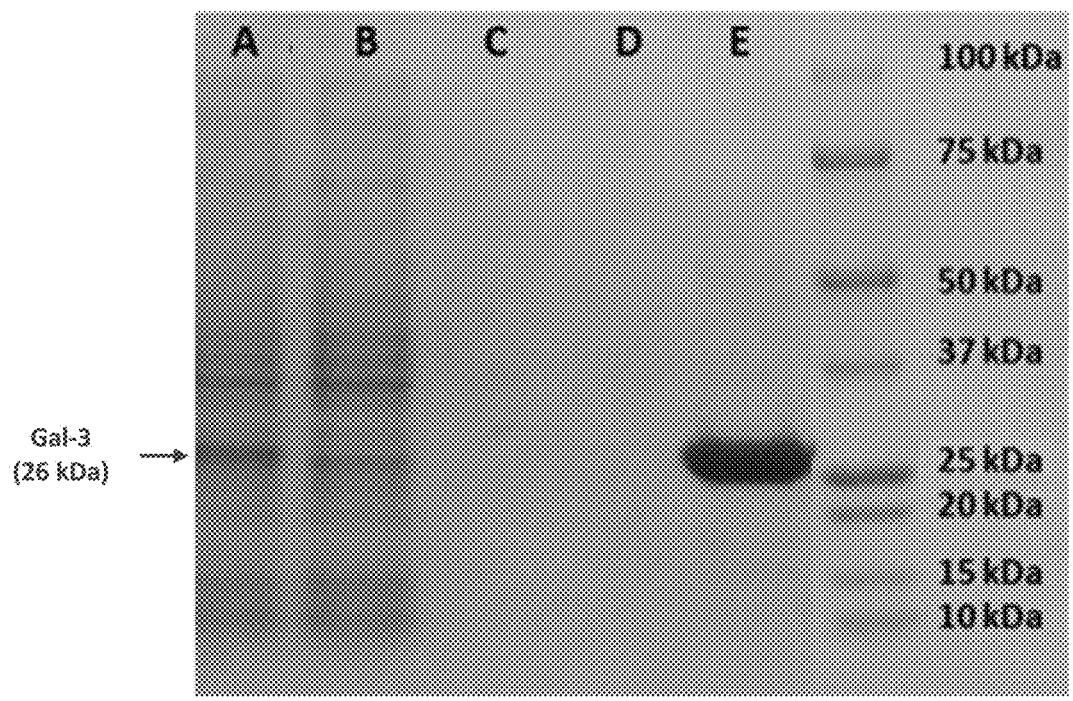
FIG. 6 depicts monitoring the purification of human galectin-3 by lactose affinity chromatography.

The results are presented in FIG. 6.

Figure 7:
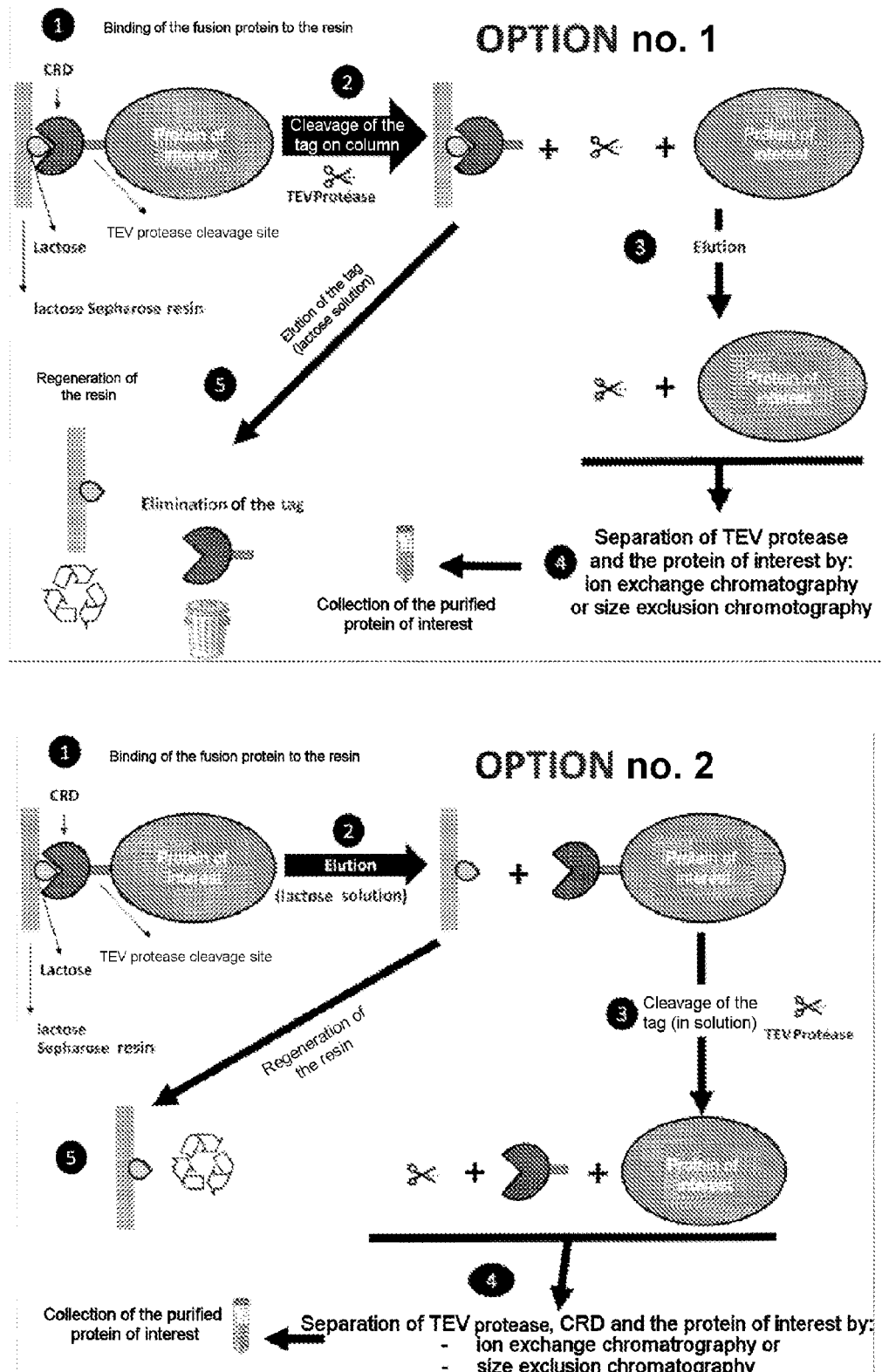
FIG. 7 depicts the diagram of the purification method of the presently disclosed subject matter by lactose affinity.

The ease with which this purification is carried out, and also the high degree of purity obtained, pointed towards the idea of developing a fusion partner (tag) intended for the purification of recombinant proteins by lactose affinity chromatography. The idea was to use a part of the lectin domain of the galectin-3 (CRD) capable of binding lactose in order to constitute this fusion partner and enable purification in a single step, during which this partner could be cleaved by TEV protease (FIG. 7).

Researching the Optimal Form of Truncated Galectin-3
Creation of the Optimized Nucleotide Sequence Encoding $CRD_{SAT}$ and Integration in an Expression Vector of pET-20b Type Starting from the nucleotide sequence of human galectin-3, 3 CRD sequences encoding 3 different CRD proteins were cloned: $CRD_{LITIL}$ (14 kDa), $CRD_{GGVVP}$ (15 kDa) and $CRD_{SAT}$ C17 kDa, natural form, non-synthetic, non-optimized) (figure. 4). As noted previously, the abbreviation "CRD", as in the "CRD domain of a galectin", refers to the highly conserved carbohydrate recognition domain of a galectin that has the ability to bind lactose. In the context of the present invention, truncated forms of the CRD domain are identified by their starting amino acid residues. Namely, the $CRD_{SAT}$ domain begins with the "SAT" sequence at amino acid residues 96-98 of SEQ ID NO: 4 and extends to the end at amino acid 250. Similarly, the $CRD_{GGVVP}$ domain begins with the "GGVVP" sequence at amino acid residues 124-128 of SEQ ID NO: 4 and extends to amino acid 250; likewise, the $CRD_{LITIL}$ domain begins with the "LITIL" sequence at amino acid residues 131-135 of SEQ ID NO: 4 and extends to amino acid 250. In the context of the fusion proteins of present invention, these CRD-based domains are collectively referred to as "lectin tags".

Figure 8:
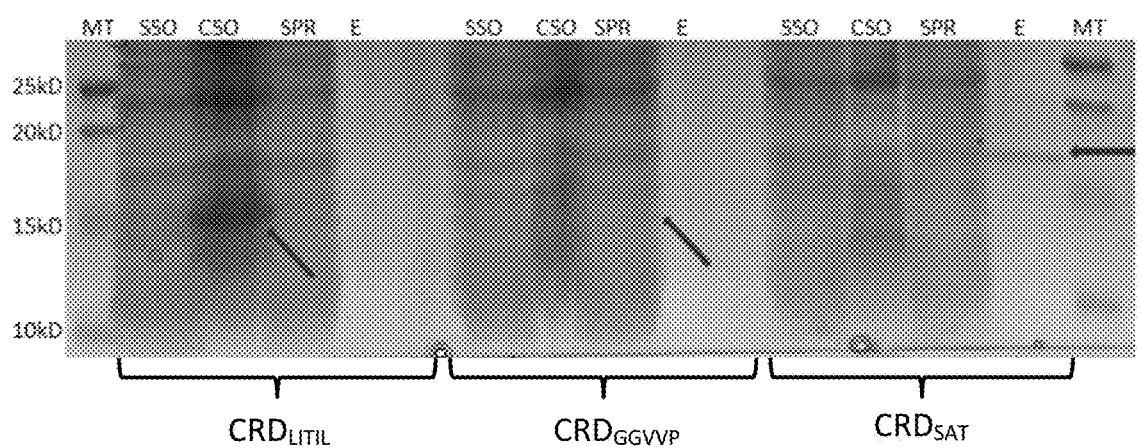
FIG. 8 depicts the follow-up purification of 3 forms of truncated human galectin-3 by lactose affinity chromatography. The $CRD_{LITIL}$ (A), $CRD_{GGVVP}$ (B), and $CRD_{SAT}$ (C) were expressed in E. coli. Rosetta 2 (DE 3) bacteria. The bacteria were lysed and purification tests were carried out on lactose-agarose column. At each purification step, a sample was taken to be run on acrylamide gel (SDS-PAGE). After electrophoretic migration, the gel was stained with Coomassie blue. SSO: sonication supernatant of bacterial extract before passage on lactose affinity column. CSO: sonication pellet of bacterial extract before passage on lactose affinity column. SPR: supernatant after passage on the lactose affinity column. E: elution fraction location of the protein of interest.

It emerges therefrom that the 3 CRDs are expressed but have varying solubility. Thus, $CRD_{LITL}$ (A) was in the totally insoluble form (in the pellet) and was not located in the eluate, and therefore was impossible to purify. $CRD_{GGVVP}$ (B) was produced in small amounts, partly in soluble form, but lost its lectin function and therefore could not be purified. $CRD_{SAT}$ (C) was produced entirely in soluble form and was able to be purified (was located in the eluate) (FIG. 8).

Given the various tests carried out, $CRD_{SAT}$ was chosen to constitute the desired fusion partner. The physicochemical characteristics of this protein, determined in silico, are as follows:

```
                              (SEQ ID NO: 1, natural form)
          10         20         30
MSATGAYPA  TGPYGAPAGP  LIVPYNLPLP  GGVVPRMLIT 40         50         60         70
ILGTVKPNAN RIALDFQRGN DVAFHFNPRF NENNRRVIVC 80         90         100        110
NTKLDNNWGR EERQSVFPFE SGKPFKIQVL VEPDHFKVAV 120        130        140        150
NDAHLLQYNH RVKKLNEISK LGISGDIDLT SASYTMI
```

Number of amino acids: 156

Molecular weight: 17 360.9 Da

Isoelectric point: 9.30

Total number of negatively-charged amino acids (Asp+Glu): 13

Total number of positively-charged amino acids (Arg+Lys): 17

Molar extinction coefficient: 12 950 $M^{-1}$ cm' (at 280 nm).

Abs 0.1% (=1 g/l) 0.746, with the proviso that all the cysteines are in reduced form.

The sequence encoding $CRD_{SAT}$ was optimized in silico in order to promote expression of this heterologous protein in *E. coli* (removal of codon bias) and to make it possible to increase the solubility thereof (substitution of arginine 36 for lysine), and also the rigidity thereof by increasing bulk (substitution of alanine 152 for threonine), thereby making it possible for the protease to cleave 14 amino acids downstream.

This optimized $CRD_{SAT}$ sequence was integrated into an expression vector of pET-20b type: the pCARGHO vector (FIG. 2), in order to enable the expression and purification of a protein of interest according to example 3.

Example 2: pCARGHO: Materials and Methods

The pCARGHO plasmid enables the production of a fusion protein may consist, in order, of: the $CRD_{SAT}$ from human galectin-3, a spacer arm enabling flexibility, a site for cleavage by TEV protease and the protein of interest.

The *E. coli* strain used should be of (DE3) type, that is to say should have the T7 RNA polymerase gene integrated into its genome.

The pCARGHO plasmid is derived from pET20b(+) from Novagen and includes the following elements (FIG. 1):

| ELEMENTS | POSITION |
| --- | --- |
| Origin of replication | 1944 |
| T7 promoter | 797-813 |
| Ribosome binding site: RBS | 742-747 |
| $CRD_{SATG}$ sequence | 242-736 |
| TEV recognition site sequence | 221-241 |
| Multiple cloning site: MCS | 159-215 |
| T7 terminator | 26-72 |
| F1 origin | 3694-4149 |
| bla ampicillin resistance gene | 2705-3562 |

The main characteristics of the pCARGHO vector are indicated in FIG. 2 (SEQ ID NOs: 2 and 3).

Cloning in the pCARGHO Plasmid

The protocol below is an example of cloning of a PCR fragment of a protein of interest in the pCARGHO vector. For some experiments (enzymatic digestion, ligation reaction, bacterial transformation), reference should especially be made to the suppliers of the reagents used.

The PCR fragment used should contain the NcoI restriction site at its 5' end and another BamHI, EcoRI, SacI, SalI, HindIII, NotI and XhoI restriction site at its 3' end. The ends may either be blunt or extended by a 3' adenosine. It should be ensured that the composition of the PCR fragment guarantees that the reading frame is abided by from the start codon ATG.

1) Digest 1 μg of pCARGHO plasmid and 1 μg of PCR fragment in parallel in 20 μl of 1× digestion buffer (10× stock) with 10 units of NcoI and 10 units of the second endonuclease chosen (depending on the site available in the MCS), at 37° C. for 1 h to 2 h. The enzymes will then be inactivated at 65° C. for 10 minutes.
2) Verify the complete digestion of the plasmid after migration on agarose gel (5 μl).
3) Purify the digested PCR fragment and plasmid, with the aim of eliminating the MCS fragment from the plasmid and the free ends from the PCR fragment. The purification may be carried out on gel and/or using specific kits.
4) Assay the plasmid and the PCR fragment (insert).
5) Prepare the following ligation mixture:
30-50 ng of the digested plasmid
50 ng of insert in 1 μl of stock ligation buffer 10×
1 μl of T4 DNA ligase
$H_2O$ q.s. to 10 μl
6) Incubate for 10 minutes to 2 h at room temperature or at 16° C. for 16 h.
7) Transform the competent cloning bacteria (TOP10, DH5a type): take off 2 μl of the ligation reaction and add 50 μl of bacteria. Incubate for 30 minutes in ice. Heat to 42° C. for 1 minute.
8) Add 200 μl of SOC (or LB) medium and incubate at 37° C. for 20 minutes to 1 h. Spread on selective agar (LB Agar, 100 μg/ml of ampicillin). Incubate overnight at 37° C.
9) Look for the presence of positive clones (verify the presence of the insert in the plasmid) by methods well known in the art such as PCR directly on colonies, minipreparation of plasmid DNA, digestion by suitable restriction enzymes and migration on agarose gel, test of overexpression of the fusion protein.
10) Sequence the plasmids extracted from the clones assumed to be positive, in order to validate the molecular cloning.

Expression of the Fusion Protein "$CRD_{SAT}$ Protein of Interest"

Test of Expression of the Fusion Protein
1) Transform competent expression bacteria [BL21(DE3) type] with the pCARGHO-X vector (X being the sequence encoding the protein of interest fused to the $CRD_{SAT}$ tag)
2) Inoculate the colonies isolated on agar in 5 ml of LB medium+ampicillin 100 µg/ml and culture until $2\times10^8$ cells/ml ($A_{600}$=0.5-0.6).
3) Divide the sample into two cultures of 2.5 ml.
4) Add IPTG into one of the cultures at a final concentration of 1 mM. Incubate both cultures at 37° C. for 2-3 h.
5) Sample 500 µl from each culture. Centrifuge at maximum speed for 1 minute, dispense with the supernatants and suspend the bacterial pellets with 100 µl of Laemmli buffer 1×.
6) Boil the samples for 1 minute. Run 10 µl of each sample and a molecular weight marker on an SDS-PAGE gel at a suitable percentage. Migrate, and reveal by staining with Coomassie Brilliant Blue for example.

Production of the Fusion Protein

Once the sequencing and the expression tests have been validated, the protein of interest fused to the $CRD_{SAT}$ tag ($CRD_{SAT}$ protein of interest) may be produced according to the procedure below.
1) Transform competent expression bacteria [BL21(DE3) type] with the pCARGHO-X vector (X being the sequence encoding the protein of interest fused to the $CRD_{SAT}$ tag). Carry out preculture in Luria Bertani LB medium+ampicillin 100 µg/ml, at 37° C. for 16 h.
2) Inoculate this preculture to 1/100th in 1 liter of rich medium of Luria Bertani LB type+ampicillin 100 µg/ml.
3) Culture at 37° C. until $2\times10^8$ cells/ml ($A_{600}$=0.5-0.6). Add IPTG at a final concentration of 1 mM. Incubate the bacteria at 37° C. with agitation for 2-3 h.
4) sample 20 µl of the crude bacterial suspension (A), centrifuge (4000 g for 20 minutes) the culture, eliminate the supernatant and suspend the bacterial pellet in 25 ml of lysis buffer.

Different adjuvants may make it possible to avoid proteolysis (ethylenediaminetetraacetic acid (EDTA), phenylmethylsulfonyl fluoride (PMSF), etc.) or oxidation (dithiothreitol (DTT), β-mercaptoethanol).
5) Place the sample in ice and lyze the bacteria using a sonicator or a French press. Sample 20 µl of this lyzed bacterial suspension (A').
6) Centrifuge the lyzed bacterial suspension at 20 000 g for 20 minutes. Recover the protein supernatant (Sp). Sample 20 µl of this supernatant (B). Dilute, where appropriate, with lysis buffer or column buffer.

Purification of the Fusion Protein "$CRD_{SAT}$ Protein of Interest"

Purification in Automatic Mode
1) After filtration over 0.45 µm membrane, inject the sample Sp on a lactose-Sepharose® resin (15 to 20 ml) equilibrated beforehand with 5 CV (column volumes) of column buffer. Sample 20 µl of the soluble fraction that has flowed through the chromatography column (C).
2) Wash the column with 10 CV of column buffer. Sample 20 µl of the washing liquid (D) at the column outlet.
3) Elute the fusion protein with 1-2 CV of column buffer and +150 mM of lactose. Collect the corresponding fractions (size of the fractions: approximately ⅕ of the volume of the column). Sample 20 µl of eluate (E).

Monitor the fusion protein present in the fractions collected, by absorption at 280 nm and/or by colorimetric methods (BCA, Bradford, etc.).

If the $CRD_{sat}$ tag would be undesirable for the subsequent applications of the protein of interest, it is possible to cleave it after elution of the fusion protein (cf. section on cleavage of the fusion protein).
4) Bring together the fractions containing the fusion protein and concentrate if necessary. Conserve the protein of interest at −80° C. after freezing in liquid nitrogen with or without addition of 30 to 50% glycerol.
5) Evaluate the quality of the purification by SDS-PAGE+ staining: dilute samples A to E to half strength in Laemmli 2× buffer then boil (95° C., 5 minutes) before migrating them on an acrylamide gel at the suitable percentage.
6) Regenerate the column with 5 CV of 2 M NaCl solution then 5 CV of water. Conserve the column in water+ ethanol 20% or in Tris-Hcl 20 mM, EDTA 1 mM.

Purification in Batch Mode
1) Deposit the sample Sp on a lactose agarose resin (10-15 ml) equilibrated beforehand with 5 to 10 CV of column buffer (Tris 20 mM, EDTA 5 mM, NaCl 150 mM, pH to be adapted depending on the protein of interest) and place under weak agitation for 1 to 2 hours. Then arrange a column with fritted disk. Sample 20 µl of the soluble fraction that has flowed through the chromatography column (C).
2) Wash the column with 10 CV of column buffer then with 10 CV of PBS buffer. Sample 20 µl at the column outlet.
3) Elute the fusion protein with 2.5 CV of PBS buffer and +150 mM of lactose.
4) Evaluate the quality of the purification, assay the fusion protein then store it according to the procedures described in the section on purification in automatic mode.
5) Regenerate the column with 10 CV of 2 M NaCl solution.

Cleavage of the Fusion Protein "$CRD_{SAT}$ Protein of Interest"

The fusion protein is cleaved by TEV protease, the cleavage site of which is located at the C-terminus of the $CRD_{SAT}$ tag. The cleavage occurs after the elution of the fusion protein and should be followed by a step of either cation exchange or size exclusion chromatography in order to separate the $CRD_{SAT}$ tag (pI=8.7, MW=18.8 kDa) and the TEV protease (pI=8.8, MW=27 kDa) from the protein of interest.
1) Dilute the concentrated solution of fusion protein to a concentration of 1-2 mg/ml in the cleavage buffer: 25 mM Tris-HCl, pH 8, 150-500 mM NaCl, 15 mM β-mercaptoethanol. Sample 20 µl of sample (A).
2) Add the TEV protease at a ratio of 1:100, i.e. 1 mg (10 000 units) of protease per 100 mg of fusion protein. The "ideal" ratio may be optimized.
3) Incubate the mixture at 4° C. overnight or else at room temperature or at 30-37° C. for shorter periods of time, the limiting factor being the stability of the protein of interest. Sample 20 µl of sample after cleavage (B).
4) Run samples A and B on SDS-PAGE gel in order to verify the effectiveness of the cleavage.

5) Eliminate the $CRD_{SAT}$ tag and also the TEV protease by:
  a) cation exchange chromatography:
    i. Dialyze or dilute the cleavage reaction mixture with the aim of lowering the ionic strength with a 20 mM Tris-HCl, 25 mM NaCl, pH 7 buffer. The salt concentration should not exceed 25 mM.
    ii. Equilibrate the SP-Sepharose® or equivalent column with 5 CV of column buffer (according to the manufacturer's recommendations).
    iii. Deposit the mixture on the column and immediately collect the fraction not retained, which contains the protein of interest (as long as the protein of interest has an acid pI (<7)).
    iv. Concentrate the protein of interest, where appropriate, and conserve it at 80° C. after freezing in liquid nitrogen with or without addition of 30 to 50% glycerol.
    v. Regenerate the column with 5 CV of 2 M NaCl buffer (elution of the $CRD_{SAT}$ tag and of the TEV protease), 5 CV of water. Conserve in water+20% ethanol.
  b) size exclusion chromatography
    i. Equilibrate the Superdex 75® or Superdex 200® or equivalent column with 2 CV of column buffer (according to the manufacturer's recommendations).
    ii. Inject the mixture on the column and collect the fractions corresponding to the protein of interest without tag [as a function of the molecular weight (size) thereof].
    iii. Concentrate the protein of interest, where appropriate, and conserve it at 80° C. after freezing in liquid nitrogen or addition of 30 to 50% glycerol.

If the tag has a molecular weight (MW) that is very different from that of the protein of interest, detection by staining the gel is sufficient. If, however, the MW thereof is very similar, more specific detection by western blot is possible using anti-$CRD_{sat}$ antibodies.
    iv. Conserve the column in water+20% ethanol.

Addendum: If TEV digestion is not carried out, and if lactose would be inappropriate for the subsequent applications of the purified protein, dialysis may be carried out or a gel filtration column may be carried out.

Example 3: Monitoring Purification of Bacterial Thioredoxin (Trx1) by Lactose Affinity Chromatography Trx1 fused to $CRD_{SAT}$ was expressed in *E. coli* Rosetta2 (DE3) bacteria according to the protocol described above.

The bacteria were lyzed and purification was carried out on lactose-agarose column according to the protocol described above.

At different purification steps, a sample was taken to be run on acrylamide gel (SDS-PAGE).

After electrophoretic migration, the gel was stained with Coomassie Brilliant Blue.

Figure 10:
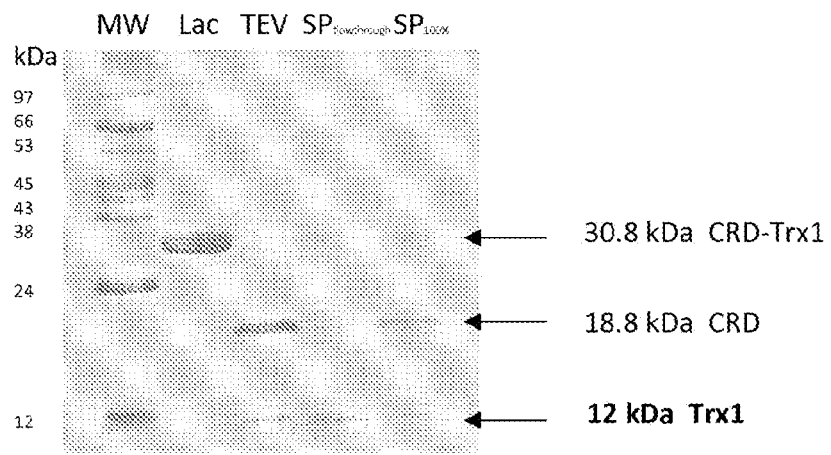
FIG. 10 depicts monitoring the purification of bacterial thioredoxin (Trx1) by lactose affinity chromatography according to the process of the presently disclosed subject matter.

The results are presented in FIG. 10.

MW: molecular weights.

Lac: purified fraction of Trx1-$CRD_{SAT}$ fusion protein on lactose-agarose resin, elution with 150 mM of lactose.

TEV: fraction after cleavage with TEV protease, to 1/100, overnight at ambient temperature.

SP flow through: fraction not retained after injection on SP Sepharose (cation exchange) column of the digestion reaction medium (TEV).

SP 100%: fraction eluted with 1 M of NaCl (SP Sepharose).

Example 4: Monitoring Purification of Human Membrane Receptor TREM-1 (Extracellular Domain) by Lactose Affinity Chromatography TREM-1 (21-136) fused to $CRD_{SAT}$ was expressed in *E. coli* C41 (DE3) bacteria according to the protocol described above.

The bacteria were lyzed and purification was carried out on lactose-agarose column according to the protocol described above.

At different purification steps, a sample was taken to be run on acrylamide gel (SDS-PAGE).

After electrophoretic migration, the gel was stained with Coomassie Brilliant Blue.

Figure 11:
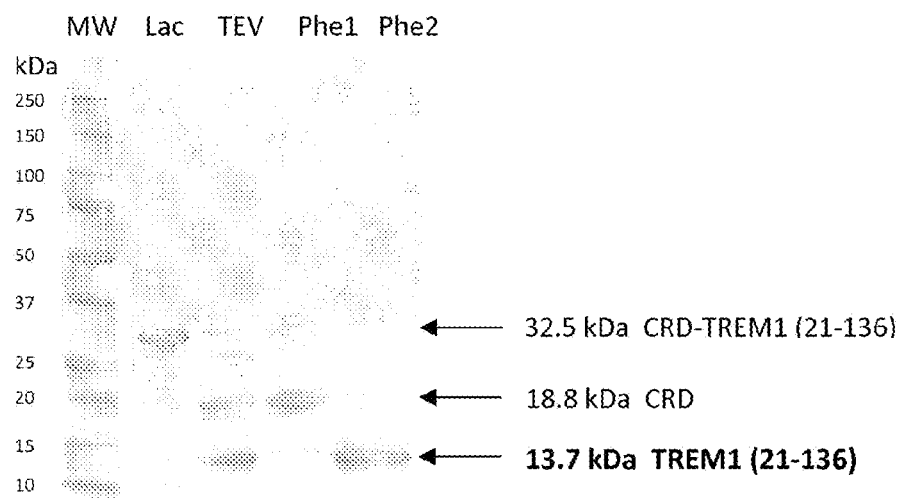
FIG. 11 depicts monitoring the purification of extracellular domain TREM-1, residues 21 to 136, by lactose affinity chromatography according to the process of the presently disclosed subject matter.

The results are presented in FIG. 11.

MW: molecular weights.

Lac: purified fraction of CRD-TREM-1(21-136) fusion protein on lactose-agarose resin, elution with 150 mM of lactose.

TEV: fraction after cleavage with TEV protease, to 1/100, overnight at ambient temperature.

Phe1: fraction not retained after injection on Phenyl Sepharose (hydrophobic interaction) column of the digestion reaction medium (TEV), containing the CRD tag.

Phe2: fraction, eluted with 300 mM of ammonium sulfate, containing TREM-1, 13.7 kDa, residues 21 to 136 with a yield of 4 mg/l of bacterial culture.

REFERENCE LIST

1. Stadtman et al., Free Radic Biol Med., 9(4):315-25, 1990
2. Chen et al., Mol Cell Biol. May; 26(10): 3728-3737, 2006
3. Andberg et al., Protein Science, 16:1751-1761, 2007
4. Ortiz-Salmeron et al., Eur. J. Biochem., 268, 4307-4314, 2001
5. International application WO 2009/121994
6. International application WO 9966053
7. Tielker et al., Biotechniques, 41(3): 327-332, 2006
8. Cooper, Biochim. & Biophys. Acta, 1572(2-3): 209-231, 2002
9. Leffler et al., Glycoconj. J., 19: 433-440, 2004
10. Ochieng et al., Biochim. Biophys. Acta, 1379: 97-106, 1998
11. Salomonsson et al., J. Biol. Chem., 285: 35079-35091, 2010
12. Seetharaman et al., J. Biol. Chem., 273: 13047-13052, 1998
13. Taylor et al., Biochem. J., 274: 575-580, 1991
14. Kelker et al., J. Mol. Biol. 342, 1237-1248, 2004
15. Radaev et al., Structure 11, 1527-1535, 2003

The invention claimed is:

1. A fusion protein, comprising: a lectin tag derived from a carbohydrate recognition domain (CRD) of a naturally occurring galectin, fused with a molecule of interest, with a site for cleavage by protease inserted between the two, wherein said lectin tag comprises the amino acid sequence of SEQ ID NO: 1.

2. The fusion protein as claimed in claim 1, wherein said lectin tag comprises the CRD$_{SAT}$ domain of galectin-3 set forth in amino acids 1 to 156 of SEQ ID NO: 3.

3. The fusion protein as claimed in claim 2, wherein the cleavage site is a site for cleavage by TEV protease.

4. A CRD$_{SAT}$ domain comprised of the amino acid sequence set forth in SEQ ID NO: 1.

5. The fusion protein as claimed in claim 1, wherein the cleavage site is a site for cleavage by TEV protease.

6. The fusion protein as claimed in claim 3, wherein said site for cleavage by TEV protease comprises amino acids 165 to 171 of SEQ ID NO:3.

7. The fusion protein as claimed in claim 3, wherein said fusion protein comprises an 8-residue spacer arm disposed between said CRD$_{SAT}$ domain of galectin-3 and said site for cleavage by TEV protease, wherein said 8-residue spacer arm is the amino acid sequence set forth in amino acids 157 to 164 of SEQ ID NO: 3.

8. A CRD$_{SAT}$ domain comprising the amino acid sequence set forth in residues 1 to 156 of SEQ ID NO: 3.

* * * * *